United States Patent
Parashar

(10) Patent No.: US 8,961,681 B2
(45) Date of Patent: Feb. 24, 2015

(54) PROCESS FOR THE PREPARATION OF NANO ZINC OXIDE PARTICLES

(75) Inventor: Sachin Parashar, Pune (IN)

(73) Assignee: TATA Chemicals Limited, Mumbai (IN)

( * ) Notice: Subject to any disclaimer, the term of this patent is extended or adjusted under 35 U.S.C. 154(b) by 581 days.

(21) Appl. No.: 12/921,734

(22) PCT Filed: Jan. 7, 2009

(86) PCT No.: PCT/IN2009/000021
§ 371 (c)(1),
(2), (4) Date: Sep. 9, 2010

(87) PCT Pub. No.: WO2009/116062
PCT Pub. Date: Sep. 24, 2009

(65) Prior Publication Data
US 2011/0002970 A1    Jan. 6, 2011

(30) Foreign Application Priority Data

Mar. 10, 2008  (IN) .......................... 480/MUM/2008
Dec. 22, 2008  (IN) ........................ 2655/MUM/2008

(51) Int. Cl.
*C04B 14/00*      (2006.01)
*C09C 1/04*       (2006.01)
(Continued)

(52) U.S. Cl.
CPC . *C01G 9/02* (2013.01); *B82Y 30/00* (2013.01); *C01G 9/003* (2013.01); *C03C 17/25* (2013.01); *C09C 1/043* (2013.01); *C01P 2004/64* (2013.01); *C01P 2006/60* (2013.01); *C03C 2217/216* (2013.01); *Y10S 977/773* (2013.01)

USPC ........ 106/425; 106/287.18; 423/622; 424/59; 424/400; 424/401; 424/642; 502/343; 977/773

(58) Field of Classification Search
USPC ........ 106/287.18, 425; 423/622; 424/59, 400, 424/401, 642; 502/343; 977/773
See application file for complete search history.

(56) References Cited

U.S. PATENT DOCUMENTS 6,255,537 B1 * 7/2001 Hayashi et al. ............... 568/622
6,710,091 B1 * 3/2004 Womelsdorf et al. ......... 423/101
(Continued)

FOREIGN PATENT DOCUMENTS

CN        1792809 A    *  6/2006
DE   102007029283 A1   * 12/2008
(Continued)

OTHER PUBLICATIONS

Khan, Myrtil L., "Size- and Shape-Control of Crystalline Zinc Oxide Nnaoparticles: A New Organometallic Synthetic Method", Advanced Functional Materials, vol. 15, No. 3 (Mar. 2005) pp. 458-468.*

(Continued)

*Primary Examiner* — Kaj K Olsen
*Assistant Examiner* — Ross J Christie
(74) *Attorney, Agent, or Firm* — Klarquist Sparkman, LLP

(57) ABSTRACT

A process for the preparation of nano zinc oxide particles is disclosed. The process comprises of dissolving a zinc metal precursor in a solvent to obtain a first solution and dissolving a base in an alcohol to obtain an alkali solution. The alkali solution is then added to the first solution over a predetermined period of time to obtain nano zinc oxide particles in solution.

13 Claims, 2 Drawing Sheets

(51) Int. Cl.
*C01G 9/02* (2006.01)
*B82Y 30/00* (2011.01)
*C01G 9/00* (2006.01)
*C03C 17/25* (2006.01)

(56) References Cited

U.S. PATENT DOCUMENTS

2003/0172845 A1* 9/2003 Marx et al. .................. 106/425
2006/0222586 A1* 10/2006 Chiang et al. ................ 423/622
2007/0004840 A1* 1/2007 Miyatake et al. ............. 524/432
2007/0140951 A1* 6/2007 O'Brien et al. ............. 423/592.1
2008/0124268 A1* 5/2008 Yang et al. .................. 423/511

FOREIGN PATENT DOCUMENTS

WO   WO 2008079800 A1 *   7/2008
WO   WO 2009085721 A1 *   7/2009
WO   WO 2009085731 A1 *   7/2009

OTHER PUBLICATIONS

Koch, U. et al., "Photochemistry of Semiconductor Colloids. Preparation of Extremely Small ZnO Particles, Fluorescence Phenomena and Size Quantization Effects," Chemical Physics Letters, vol. 122, No. 5, pp. 507-510 (Dec. 20, 1985).

Hsieh, C., "Spherical Zinc Oxide Nano Particles from Zinc Acetate in the Precipitation Method," Journal of the Chinese Chemical Society, vol. 54, No. 1, pp. 31-34 (2007).

\* cited by examiner

PROCESS FOR THE PREPARATION OF NANO ZINC OXIDE PARTICLES

CROSS-REFERENCE TO RELATED APPLICATIONS

This application is a filing under 35 U.S.C. §371 based on PCT/IN2009/000021 filed Jan. 7, 2009, which claims priority to Indian Patent Applications No. 480/MUM/2008 filed Mar. 10, 2008, and 2655/MUM/2008 filed Dec. 22, 2008, each of which applications are incorporated herein in their entirety.

FIELD

The invention relates to a process for preparing nano particles. More particularly the invention relates to a process for the preparation of nano zinc oxide particles.

DESCRIPTION OF RELATED ART

Zinc Oxide is used for various purposes including as a white pigment, as a catalyst, as a constituent of anti-bacterial skin protection ointment, sunscreens and wood varnishes. Zinc oxide is also known as wide band gap semiconductor and is well suited for emissive devices. Materials used for blocking UV radiation are required to be transparent to the visible part of the solar radiation while blocking the harmful UV radiation and nano zinc oxide is considered favorable in this regard. The term 'nano' or 'nano particle' is generally used to refer to particles having one of the dimensions of less than about 100 nm.

Though numerous processes are known for the synthesis of nano zinc oxide particles, such processes are not scalable in an efficient manner and do not produce free flowing nano zinc oxide particle powders. This limitation is often a significant deterrent in the commercialization of nano zinc oxide particles.

The essential process for the synthesis of nano zinc oxide is a basic alcoholic hydrolysis of zinc metal precursor and most known processes describe the synthesis of nano zinc oxide particles in an alcohol or an alcohol-water mixture as the medium of reaction. Such processes involve dissolving the metal precursor by heating or boiling the alcohol with reactions carried out at elevated temperatures. As these families of precursors have poor solubility in alcohols; the processes require heating them to high temperatures, typically the boiling points in the case of alcohols. Examples of such processes may be found in U.S. Pat. No. 6,710,091; US2006/0222586; US2003/0172845; and in Koch et. al Chemical Physics Letters, 122-507, 1985.

It would be useful to identify a process by which free flowing nano zinc oxide particles may be formed and that such a process be scalable to allow for large scale production of nano zinc oxide particles.

SUMMARY

The invention relates to a process for the preparation of nano zinc oxide particles comprising dissolving a zinc metal precursor in a solvent to obtain a first solution; dissolving a base in an alcohol to obtain an alkali solution; and adding the alkali solution to the first solution over a predetermined period of time to obtain nano zinc oxide particles in dispersion.

In accordance with an aspect of the invention the dispersion containing nano zinc oxide particles is refrigerated to allow for stable storage.

In accordance with an aspect of the invention a non solvent is added to the dispersion to precipitate nano zinc oxide particles in solution.

In accordance with an aspect of the invention the solution so obtained by adding a non solvent is further processed for the extraction of nano zinc oxide particles comprising transferring the solution containing nano zinc oxide particles to a separating means for settling the nano zinc oxide particles, removing the settled nano zinc oxide particles from the separating means and centrifuging and drying the nano zinc oxide particles so removed to obtain dry nano zinc oxide particles.

The invention also relates to a process for the preparation of nano zinc oxide particles comprising dissolving zinc acetate dihydrate $\{Zn(OAc)_2\}$ in N,N dimethyl formamide [DMF] to obtain a first solution; dissolving a base in alcohol to obtain an alkali solution; and adding the alkali solution to the first solution over a predetermined period of time to obtain nano zinc oxide particles.

In accordance with an aspect of the invention the base is sodium hydroxide and the alcohol is ethanol.

In accordance with an aspect of the invention the centrifuged nano zinc oxide particles are dried over phosphorous pentaoxide in a vacuum desiccator.

The invention relates to a process for the preparation of nano zinc oxide particles comprising dissolving zinc acetate dihydrate $\{Zn(OAc)_2\}$ in N,N dimethyl formamide [DMF] to obtain a first solution; dissolving sodium hydroxide in ethanol to obtain an alkali solution; adding the alkali solution to the first solution over a predetermined period of time to obtain nano zinc oxide particles in dispersion; adding acetone to the dispersion to precipitate nano zinc oxide particles; transferring solution containing nano zinc oxide particles to a separating means to allow the nano zinc oxide particles to settle; removing the settled nano zinc oxide particles from the separating means; decanting excess solution present in the nano zinc oxide particles removed from the separating means; and centrifuging the nano zinc oxide particles.

The invention relates to a process for the preparation of capped nano zinc oxide particles including dissolving a zinc precursor in a solvent to obtain a first solution, adding a capping agent to the first solution, dissolving a base in an alcohol to obtain an alkali solution, and adding the alkali solution to the first solution over a predetermined period of time to obtain capped nano zinc oxide particles, wherein the quantity of the alkali solution added is at least 5% in excess to the quantity of the alkali solution required for a molar reaction.

In accordance with an aspect the quantity of the alkali solution added is between 5% to 40% in excess to the quantity of the alkali solution required for a molar reaction.

DESCRIPTION OF ACCOMPANYING DRAWINGS

The accompanying drawings illustrate the preferred embodiments of the invention and together with the following detailed description serve to explain the principles of the invention.

DETAILED DESCRIPTION

Figure 1:
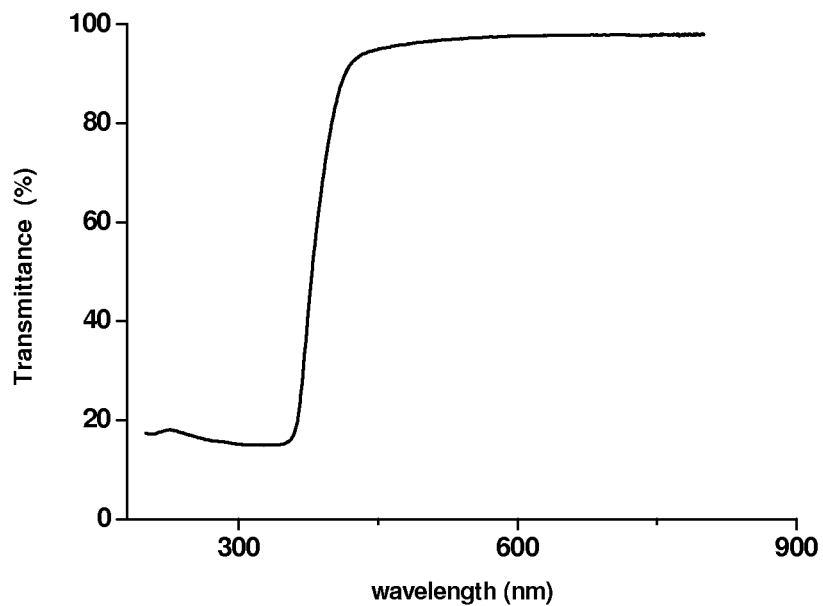
FIG. 1 illustrates the transmittance at different wavelengths of the solar spectrum for a sample of nano zinc oxide particles formed for the acetone precipitated reaction with 1:1 molar alkali addition, achieving a 100 percent reaction completion.

For the purpose of promoting an understanding of the principles of the invention, reference will now be made to the embodiment described and specific language will be used to describe the same. It will nevertheless be understood that no limitation of the scope of the invention is thereby intended, such alterations and further modifications in the process, and such further applications of the principles of the invention therein being contemplated as would normally occur to one skilled in the art to which the invention relates.

It will be understood by those skilled in the art that the foregoing general description and the following detailed description are exemplary and explanatory of the invention and are not intended to be restrictive thereof.

A method to synthesize nano zinc oxide particles in a single-phase organic medium is disclosed. The process in accordance with the principles of the invention preferably involves dissolving the zinc metal precursor in a solvent followed by the addition of a basic-alcohol solution to obtain nano zinc oxide particles. More specifically, the process involves dissolving the zinc metal precursor in a solvent such as N,N dimethylformamide (DMF) to obtain a first solution, dissolving a base in an alcohol to obtain an alkali solution, and the addition of the alkali solution to the first solution to obtain nano zinc oxide particles.

The following description refers to certain specific compounds such as alcohols, bases; solvents and non solvents to explain the principles of the invention. The invention however is not restricted to such compounds as any equivalent chemical compound may be utilized to achieve the desired end result as taught by the invention.

In the following description zinc acetate dihydrate has been employed as the source of zinc while the solvent employed is N,N dimethylformamide (DMF). The zinc acetate dihydrate is dissolved in N,N dimethylformamide (DMF) to obtain a first clear solution. A second solution is prepared independently by dissolving sodium hydroxide in ethanol to get an alkali solution. The alkali solution is added to the zinc acetate solution in a controlled manner and over a predetermined period of time to ensure that only nano zinc oxide particles are formed.

To precipitate or cause sedimentation of the nano zinc oxide particles a non-solvent such as acetone, hexane, heptane and toluene, or any similar members of their family, or any combination of them is preferably added to the reaction mixture. On the addition of the non-solvent the nano zinc oxide particles eventually settle down.

It is preferred that the manner of addition of the alkali solution to the first solution is not a dumping operation, but spread over a period of time that is appropriate to dehydrate the zinc hydroxide formed after the addition of the alkali solution, such that nano zinc oxide particles in dispersion are obtained. Preferably such process may be executed by adding the alkali at a rate of approximately 1% of alkali a minute continuously, or alternatively by adding predetermined amounts of the alkali at specific intervals spread apart by a predetermined period, such as a time interval of 5 to 10 minutes and adding 5% to 10% of the alkali at each interval. Accordingly the process of addition may be spread over 50 to 100 minutes depending on the percentage of reaction completion required to get appropriate particle size and yield.

The base used for the preparation of the alkali solution may be any $OH^-$ or $NH^-$ group containing basic compound particularly an alkali metal one like NaOH, KOH, LiOH, tetramethylammonium hydroxide or any other member of the similar family, preferably sodium hydroxide.

The alcohol may be a monoalcohol or polyalcohol particularly ethanol, methanol, propanol or any other member of the alcohol family, preferably ethanol The reactions involved in the process may be summarized as:

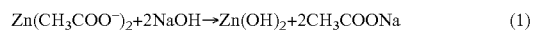

$$Zn(CH_3COO^-)_2 + 2NaOH \rightarrow Zn(OH)_2 + 2CH_3COONa \qquad (1)$$

$$Zn(OH)_2 \rightarrow ZnO + H_2O \qquad (2)$$

As shown by equation 1, zinc acetate reacts with sodium hydroxide to provide zinc hydroxide and sodium acetate. The zinc hydroxide is dehydrated to provide nano zinc oxide and water.

In accordance with an aspect of the invention, a process for the extraction of the nano zinc oxide particles at industrial scale is disclosed. The use of non solvent for precipitation of the nano particles provides for a simple way to extract particles at high throughput. The process involves sedimentation followed by decantation, centrifugation and finally drying of nano particles over phosphorus pentaoxide in a vacuum desiccator.

The nano particles are obtained early on in the process as dispersion. Subsequent processing is done to this dispersion to obtain nano zinc oxide particles as dry powder. The dispersion so obtained containing nano zinc oxide particles is extremely stable under refrigeration. In accordance with an aspect, the dispersion may be used for applying ultra violet coatings on glass, metals and wood etc. The dispersion may be applied directly as a thin coating on glass. As the dispersion is transparent the films applied to glass are also transparent. Moreover, the dispersion in solvent such as DMF is very stable and the process of preparing the dispersion is economical and provides significant advantages in subsequent glass coating.

In accordance with an aspect, the dispersion so prepared may be transferred to a glass manufacturing facility under refrigeration or maybe prepared at the glass manufacturing facility.

The refrigeration temperatures may be kept preferably between 0 C to 4 C or even below.

In accordance with an aspect, it is preferred that on completion of the addition of the alkali solution to the zinc acetate solution, the reaction mixture is stirred to ensure that the reaction is complete and that all the zinc acetate is converted to nano zinc oxide. The formation of nano zinc oxide particles may be monitored by doing intermediate UV visible spectroscopy.

In accordance with an aspect, the solution containing nano zinc oxide particles is transferred to a separating means to allow the nano zinc oxide particles to settle; removing the settled nano zinc oxide particles from the separating means; decanting excess solution present in the nano zinc oxide particles removed from the separating means; and centrifuging the nano zinc oxide particles.

The separating means may for example be a separating funnel. The centrifuged nano zinc oxide particles may be vacuum dried over phosphorus pentaoxide.

FIG. 1 illustrates one method of determining reaction completion. An analysis of the reaction mixture indicates that the transmittance is below 20% after approximately 360 nm. This is assumed as a 100% reaction completion.

In accordance with an embodiment, the process may be used to obtain capped nano zinc oxide particle powders. The cappant is preferably added to the metal precursor, such as the zinc acetate solution, prior to the addition of the alkali solution that allows for capping the nano zinc oxide particles as soon as they are formed. Any known organic and inorganic molecules including alkylamines like octylamine, dodecylamine, hexadecylamine; polyvinyl pyrrolidone (PVP), alkanethiols, carboxylic acids, phosphines, substituted phosphines, phosphine oxides and substituted phosphine oxides may be employed for capping the nano zinc oxide particles. The process allows for the introduction of a cappant without requiring any alteration or modification to the basic process for the production of nano zinc oxide particles.

Figure 2:
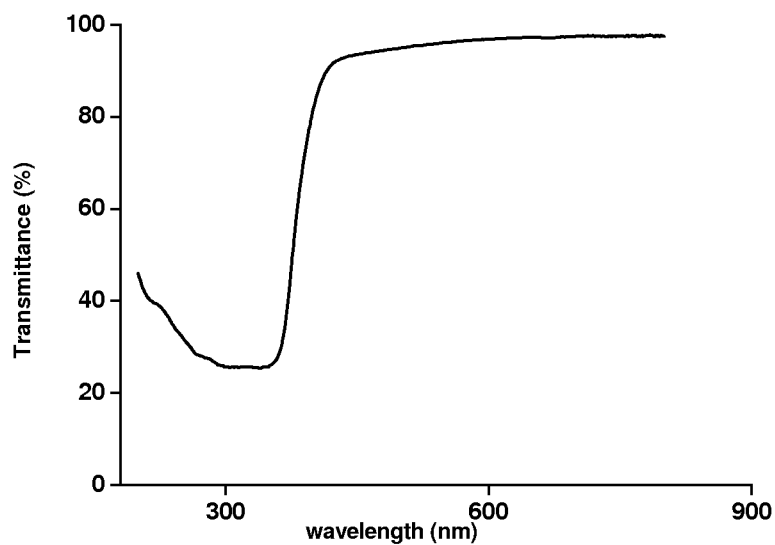
FIG. 2 illustrates the transmittance at different wavelengths of the solar spectrum for a sample of octylamine capped nano zinc oxide particles formed by addition of alkali solution required for a molar reaction (1:1 molar alkali addition).

It is observed that a 100% complete reaction is not achieved during the formation of capped nano zinc oxide particles, as illustrated in FIG. 2 where it is observed that the transmittance at certain wavelengths below 360 nm is above 20% and reaches almost 50% at certain wavelengths. This indicates a partially competed reaction.

A method to synthesize capped nano zinc oxide particles in a single-phase organic medium is disclosed. The process in accordance with the principles of the invention involves dissolving the zinc metal precursor in a solvent to obtain a zinc metal precursor solution, adding to the zinc metal precursor solution a capping agent, followed by the addition of a basic-alcohol solution to obtain capped nano zinc oxide particles, the quantity of basic-alcohol solution added to the metal precursor solution is in excess of the quantity required for a molar reaction.

More specifically, the process involves dissolving the zinc metal precursor in a solvent such as N,N dimethylformamide (DMF) to obtain a first solution, adding a capping agent to the first solution, dissolving a base in an alcohol to obtain an alkali solution, and adding the alkali solution to the first solution to obtain capped nano zinc oxide particles; the quantity of the alkali solution added to the first solution is at least 5% in excess of the quantity of the alkali solution required for a molar reaction.

In the following description zinc acetate dihydrate {Zn(OAc)$_2$} has been employed as the source of zinc while the solvent employed is N,N dimethylformamide (DMF). The zinc acetate dihydrate is dissolved in N,N dimethylformamide (DMF) to obtain a first clear solution. To the first clear solution a capping agent is added. A second solution is prepared independently by dissolving sodium hydroxide (NaOH) in ethanol to get an alkali solution. The alkali solution is added to the zinc acetate solution in a controlled manner and over a predetermined period of time to ensure that only capped nano zinc oxide particles are formed. The quantity of the alkali solution added to the zinc acetate solution is at least 5% in excess of the quantity of the alkali solution required for a molar reaction.

In accordance with an embodiment the capped nano zinc oxide particles that are formed are precipitated out slowly as the reaction proceeds. In such reactions the capping agent acts as a precipitating agent as well as surface modifier.

In accordance with an alternate embodiment to precipitate or cause sedimentation of the capped nano zinc oxide particles a non-solvent such as acetone, hexane, heptane and toluene, or any similar members of their family, or any combination of them is preferably added to the reaction mixture. On the addition of the non-solvent the capped nano zinc oxide particles eventually settle down.

The quantity of alkali solution added to the zinc metal precursor solution is in excess of the quantity of alkali solution that is required for a molar reaction. In accordance with an aspect the quantity of alkali solution that is added in excess is between 5 to 40% of the quantity of alkali solution that is required for a molar reaction.

The exactly molar process allows for the continuous production of the nano zinc oxide particles and thus enables the large scale production of nano zinc oxide particles.

The dissolving of the zinc metal precursor in DMF provides for significant advantages including no requirement of heating the reaction mixture, easily scalable process for high concentrations, the production of dry nano zinc oxide particles at high throughput and a narrow particle distribution.

The high solubility of the zinc metal precursor in DMF at room temperature allows for high production rate of nano zinc oxide particles.

The nano zinc oxide particles obtained are perfectly dry powder which is a significant advantage of the process. Moreover, the final product is an odorless, white free flowing nano zinc oxide particle powder. UV visible spectroscopy on the final product in the dry powder form indicated that all powders are transparent to visible radiation and block the UV radiation. A TEM on the powders indicated that the particle size varies between 5 nm to 50 nm depending upon the concentration and reaction completion done. The entire synthesis process is carried out at room temperature.

The simplicity of the process, particularly the absence of any heating requirements and the perfectly molar reactions, involving stirring and decantation operations, allows the process to be easily scaled up to any volume.

By way of a example, the nano zinc oxide particles obtained by the process as described herein may be used for preparation of white pigment, as a catalyst, as a constituent of anti-bacterial skin protection ointment, for preparation of sunscreen lotion, in varnishes or for ultraviolet coating of glass.

In accordance with an aspect, the nano zinc oxide particles obtained by the process as described herein are stable as dispersion in ethylene glycol and water.

The following examples are provided to explain and illustrate certain preferred embodiments of the process of the invention.

Example 1

65.847 grams of Zn(OAc)$_2$ was dissolved in 3 L of DMF to obtain the first solution. 12 grams of NaOH was dissolved in 1.5 L of ethanol, to obtain the alkali solution. 1.2 L of the alkali solution was slowly added to the first solution in order to synthesize nano zinc oxide particles. After the addition is complete, the reaction mixture is stirred for some more time. To this solution of nano zinc oxide particles 18 L of acetone was added in order to precipitate out the nano zinc oxide particles. The solution turned milky white on addition of acetone. This solution is then transferred to separating funnels so that particles settle down. Later on these settled particles are removed from the funnels. The excess solvent from the removed particles is decanted out and the remaining milky solution is centrifuged. The wet solid obtained is dried over phosphorus pentaoxide in vacuum desiccators.

Example 2

54.87 grams of Zn(OAc)$_2$ was dissolved in 2.5 L of DMF to obtain the first solution. 16 grams of NaOH was dissolved in 2 L of ethanol, to obtain the alkali solution. 1.875 L of the alkali solution was slowly added to the first solution in order to synthesize nano zinc oxide particles. After the addition is complete, the reaction mixture is stirred for some more time. To this solution of nano zinc oxide particles 17.5 L of acetone was added in order to precipitate out the nano zinc oxide particles. The solution turned milky white on addition of acetone. This solution is than transferred to separating funnels so that particles settle down. Later on these settled particles are removed from the funnels. The excess solvent from the removed particles is decanted out and the remaining milky solution is centrifuged. The wet solid obtained is dried over phosphorus pentaoxide in vacuum desiccators Example 3

54.87 grams of Zn(OAc)$_2$ was dissolved in 2.5 L of DMF to obtain the first solution. 16 grams of NaOH was dissolved in 2 L of ethanol, to obtain the alkali solution. 1.875 L of the alkali solution was slowly added to the first solution in order to synthesize nano zinc oxide particles. After the addition is complete, the reaction mixture is stirred for some more time. To this solution of nano zinc oxide particles 6.56 L of acetone was added in order to precipitate out the nano zinc oxide particles. The solution turned milky white on addition of acetone. This solution is then transferred to separating funnels so that particles settle down. Later on these settled particles are removed from the funnels. The excess solvent from the removed particles is decanted out and the remaining milky solution is centrifuged. The wet solid obtained is dried over phosphorus pentaoxide in vacuum desiccators Example 4

54.87 grams of Zn(OAc)$_2$ was dissolved in 2.5 L of DMF to obtain the first solution. 20 grams of NaOH was dissolved in 2.5 L of ethanol, to obtain the alkali solution. 2.250 L of the alkali solution was slowly added to the first solution in order to synthesize nano zinc oxide particles. After the addition is complete, the reaction mixture is stirred for some more time. To this solution of nano zinc oxide particles 7.125 L of acetone was added in order to precipitate out the nano zinc oxide particles. The solution turned milky white on addition of acetone. This solution is then transferred to separating funnels so that particles settle down. Later on these settled particles are removed from the funnels. The excess solvent from the removed particles is decanted out and the remaining milky solution is centrifuged. The wet solid obtained is dried over phosphorus pentaoxide in vacuum desiccators Example 5

109.74 grams of Zn(OAc)$_2$ was dissolved in 2.5 L of DMF to obtain the first solution. 40 grams of NaOH was dissolved in 2.5 L of ethanol, to obtain the alkali solution. 2.250 L of the alkali solution was slowly added to the first solution in order to synthesize nano zinc oxide particles. After the addition is complete, the reaction mixture is stirred for some more time. To this solution of nano zinc oxide particles 7.125 L of acetone was added in order to precipitate out the nano zinc oxide particles. The solution turned milky white on addition of acetone. This solution is then transferred to separating funnels so that particles settle down. Later on these settled particles are removed from the funnels. The excess solvent from the removed particles is decanted out and the remaining milky solution is centrifuged. The wet solid obtained is dried over phosphorus pentaoxide in vacuum desiccators Example 6

164.61 grams of Zn(OAc)$_2$ was dissolved in 2.5 L of DMF to obtain the first solution. 60 grams of NaOH was dissolved in 2.5 L of ethanol, to obtain the alkali solution. 2.250 L of the alkali solution was slowly added to the first solution in order to synthesize nano zinc oxide particles. After the addition is complete, the reaction mixture is stirred for some more time. To this solution of nano zinc oxide particles 7.125 L of acetone was added in order to precipitate out the nano zinc oxide particles. The solution turned milky white on addition of acetone. This solution is then transferred to separating funnels so that particles settle down. Later on these settled particles are removed from the funnels. The excess solvent from the removed particles is decanted out and the remaining milky solution is centrifuged. The wet solid obtained is dried over phosphorus pentaoxide in vacuum desiccators.

Example 7

21.94 grams of Zn(OAc)$_2$ was dissolved in 1.0 L of DMF to obtain the first solution. 8 grams of NaOH was dissolved in 1.0 L of ethanol, to obtain the alkali solution. 37.07 grams of dodecylamine (DDA) was added to 300 ml toluene and this solution was added to the first solution. 0.9 L of the alkali solution was slowly added to the first solution in order to synthesize nano zinc oxide particles. The solution turned milky white on addition of the base due to formation and precipitation of DDA capped nano zinc oxide particles. After the addition is complete, the reaction mixture is stirred for some more time. This solution is then transferred to separating funnels so that particles settle down. Later on these settled particles are removed from the funnels. The excess solvent from the removed particles is decanted out and the remaining milky solution is centrifuged. The wet solid obtained is dried over phosphorus pentaoxide in vacuum desiccators Example 8

21.94 grams of Zn(OAc)$_2$ was dissolved in 1.0 L of DMF to obtain the first solution. 8 grams of NaOH was dissolved in 1.0 L of ethanol, to obtain the alkali solution. 25.8 grams of octylamine (OA) was added to the first solution. 0.9 L of the alkali solution was slowly added to the first solution in order to synthesize nano zinc oxide particles. The solution turned milky white on addition of the base due to formation and precipitation of OA capped nano zinc oxide particles. After the addition is complete, the reaction mixture is stirred for some more time. This solution is then transferred to separating funnels so that particles settle down. Later on these settled particles are removed from the funnels. The excess solvent from the removed particles is decanted out and the remaining milky solution is centrifuged. The wet solid obtained is dried over phosphorus pentaoxide in vacuum desiccators.

Example 9

43.898 grams of Zn(OAc)$_2$ was dissolved in 2.0 L of DMF to obtain the first solution. 17.6 grams of NaOH was dissolved in 2.2 L of ethanol, to obtain the alkali solution. 51.7 grams of octylamine (OA) was added to the first solution. 2.0 L of the alkali solution was slowly added to the first solution in order to synthesize nano zinc oxide particles. The solution turned milky white on addition of the base due to formation and precipitation of OA capped nano zinc oxide particles. After the addition is complete, the reaction mixture was stirred for some more time. This solution is then transferred to separating funnels so that particles settle down. Later on these settled particles are removed from the funnels. The excess solvent from the removed particles is decanted out and the remaining milky solution is centrifuged. The wet solid obtained is dried over phosphorus pentaoxide in vacuum desiccators.

Example 10

Figure 3:
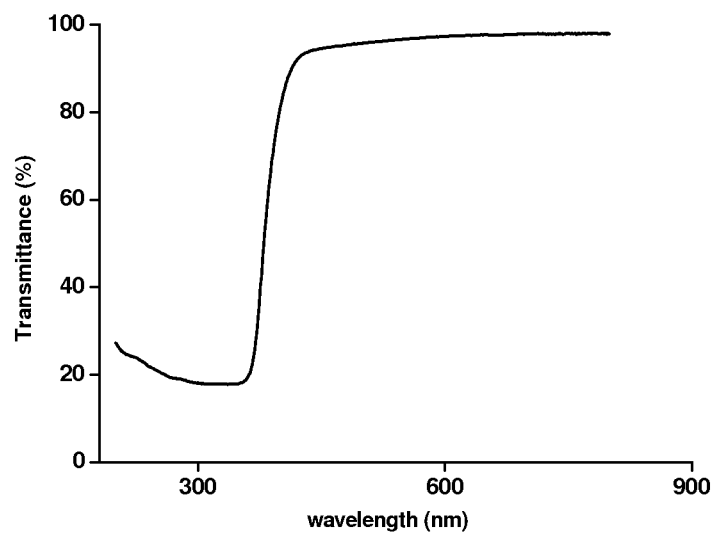
FIG. 3 illustrates the transmittance at different wavelengths of the solar spectrum for a sample of octylamine capped nano zinc oxide particles formed by addition of 5% excess alkali solution than that is required for a molar reaction (1:1.05 molar alkali addition).

219.49 grams of $Zn(OAc)_2$ was dissolved in 2.0 L of DMF to obtain the first solution. 88 grams of NaOH was dissolved in 2.2 L of ethanol, to obtain the alkali solution. 129.25 grams of octylamine (OA) was added to the first solution. 2.1 L of the alkali solution was slowly added to the first solution in order to synthesize capped nano zinc oxide particles. The solution turned milky white on addition of the base due to formation and precipitation of OA capped nano zinc oxide particles. After the addition is complete, the reaction mixture is stirred for some more time. This solution is then transferred to separating funnels so that particles settle down. The settled particles are removed from the funnels. The excess solvent from the removed particles is decanted out and the remaining milky solution is centrifuged. The wet solid obtained is dried over phosphorus pentaoxide in vacuum desiccators. FIG. 3 illustrates the transmittance at different wavelengths of the solar spectrum for a sample of octylamine capped nano zinc oxide particles formed by addition of 5% alkali solution in excess of the quantity of alkali solution required for a molar reaction.

Example 11

Figure 4:
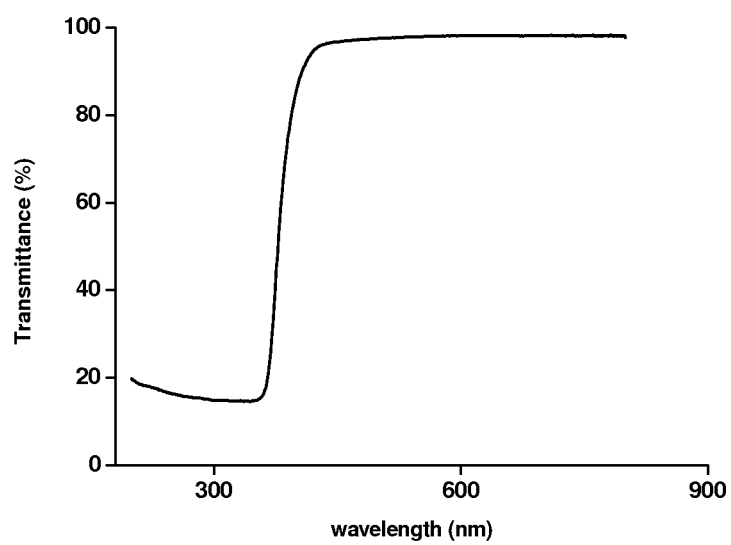
FIG. 4 illustrates the transmittance at different wavelengths of the solar spectrum for a sample of octylamine capped nano zinc oxide particles formed by addition of 10% excess alkali solution than that is required for a molar reaction (1:1.1 molar alkali addition).

219.49 grams of $Zn(OAc)_2$ was dissolved in 2.0 L of DMF to obtain the first solution. 96 grams of NaOH was dissolved in 2.4 L of ethanol, to obtain the alkali solution. 129.25 grams of octylamine (OA) was added to the first solution. 2.2 L of the alkali solution was slowly added to the first solution in order to synthesize capped nano zinc oxide particles. The solution turned milky white on addition of the base due to formation and precipitation of OA capped nano zinc oxide particles. After the addition is complete, the reaction mixture is stirred for some more time. This solution is then transferred to separating funnels so that particles settle down. The settled particles are removed from the funnels. The excess solvent from the removed particles is decanted out and the remaining milky solution is centrifuged. The wet solid obtained is dried over phosphorus pentaoxide in vacuum desiccators. FIG. 4 illustrates the transmittance at different wavelengths of the solar spectrum for a sample of octylamine capped nano zinc oxide particles formed by addition of 10% alkali solution in excess of the quantity of alkali solution required for a molar reaction.

I claim:

1. A room temperature process for the preparation of capped nano zinc oxide particles, comprising:
    dissolving a zinc metal precursor in N, N dimethyl formamide to obtain a first solution;
    adding a capping agent to the first solution;
    dissolving a base in an alcohol to obtain an alkali solution; and
    adding a quantity of the alkali solution to the first solution over a predetermined period of time to obtain capped nano zinc oxide particles in dispersion, wherein the quantity of the alkali solution added is between 5% to 40% in excess to the quantity of the alkali solution required for a molar reaction.

2. A room temperature process as claimed in claim 1 wherein the dispersion containing capped nano zinc oxide particles is refrigerated to allow for stable storage.

3. A room temperature process as claimed in claim 1 further comprising adding a non-solvent to the reaction mixture of the first solution and the alkali solution to precipitate capped nano zinc oxide particles in solution.

4. A room temperature process as claimed in claim 3, comprising:
    transferring the solution containing capped nano zinc oxide particles to a separating means for settling the capped nano zinc oxide particles;
    removing the settled capped nano zinc oxide particles from the separating means; and
    centrifuging and drying the capped nano zinc oxide particles so removed to obtain dry capped nano zinc oxide particles.

5. A room temperature process as claimed in claim 1 wherein the zinc metal precursor is zinc acetate dehydrate.

6. A room temperature process as claimed in claim 5 wherein the base is sodium hydroxide.

7. A room temperature process as claimed in claim 5 wherein the alcohol is ethanol.

8. A room temperature process as claimed in claim 1 comprising adding acetone to the reaction mixture of the first solution and the alkali solution to precipitate capped nano zinc oxide particles in solution.

9. A room temperature process as claimed in claim 1 comprising adding the capping agent to the first solution prior to adding the alkali solution to the first solution.

10. A room temperature process as claimed in claim 8 further comprising:
    transferring the dispersion containing capped nano zinc oxide particles to a separating means to allow the capped nano zinc oxide particles to settle;
    removing settled capped nano zinc oxide particles from the separating means;
    decanting excess solution present in the capped nano zinc oxide particles removed from the separating means; and
    centrifuging the capped nano zinc oxide particles.

11. A room temperature process as claimed in claim 8 wherein centrifuged capped nano zinc oxide particles are dried over phosphorous pentaoxide in a vacuum desiccator.

12. A room temperature process for the preparation of capped nano zinc oxide particles, comprising:
    dissolving zinc acetate dihydrate in N,N dimethyl formamide to obtain a first solution;
    adding a capping agent to the first solution;
    dissolving sodium hydroxide in ethanol to obtain an alkali solution;
    adding a quantity of the alkali solution to the first solution over a predetermined period of time to obtain capped nano zinc oxide particles in solution, wherein the quantity of the alkali solution added is between 5% to 40% in excess to the quantity of the alkali solution required for a molar reaction;
    adding acetone to the solution to precipitate capped nano zinc oxide particles;
    transferring solution containing capped nano zinc oxide particles to a separating means to allow the capped nano zinc oxide particles to settle;

removing settled capped nano zinc oxide particles from the separating means;
decanting excess solution present in the capped nano zinc oxide particles removed from the separating means; and
centrifuging the capped nano zinc oxide particles.

13. A room temperature process for the preparation of capped nano zinc oxide particles, comprising:
dissolving zinc acetate dihydrate in N,N dimethyl formamide to obtain a first solution;
adding octylamine to the first solution;
dissolving sodium hydroxide in ethanol to obtain an alkali solution;
adding the alkali solution to the first solution over a predetermined period of time to obtain capped nano zinc oxide particles; wherein the quantity of the alkali solution added is at least 5% in excess to the quantity of the alkali solution required for a molar reaction;
adding acetone to the solution to precipitate capped nano zinc oxide particles;
transferring solution containing capped nano zinc oxide particles to a separating means to allow the capped nano zinc oxide particles to settle;
removing the settled capped nano zinc oxide particles from the separating means;
decanting excess solution present in the capped nano zinc oxide particles removed from the separating means; and
centrifuging the capped nano zinc oxide particles.

* * * * *